US009612226B2

(12) United States Patent
Takeda et al.

(10) Patent No.: US 9,612,226 B2
(45) Date of Patent: Apr. 4, 2017

(54) METHOD FOR MEASURING HEIGHT OF LACK OF PENETRATION AND ULTRASONIC FLAW DETECTOR

(71) Applicants: IHI Infrastructure Systems Co., Ltd., Osaka (JP); IHI Corporation, Tokyo (JP)

(72) Inventors: Yuji Takeda, Osaka (JP); Takahiro Yamagami, Osaka (JP); Kunio Yonekura, Osaka (JP); Hiroaki Hatanaka, Tokyo (JP); Hiroki Kawai, Tokyo (JP); Arisa Yanagihara, Tokyo (JP)

(73) Assignees: IHI Infrastructure Systems Co., Ltd., Osaka (JP); IHI Corporation, Tokyo (JP)

( * ) Notice: Subject to any disclaimer, the term of this patent is extended or adjusted under 35 U.S.C. 154(b) by 179 days.

(21) Appl. No.: 14/418,060

(22) PCT Filed: Jul. 31, 2013

(86) PCT No.: PCT/JP2013/004637
§ 371 (c)(1),
(2) Date: Jan. 28, 2015

(87) PCT Pub. No.: WO2014/020910
PCT Pub. Date: Feb. 6, 2014

(65) Prior Publication Data
US 2015/0300992 A1 Oct. 22, 2015

(30) Foreign Application Priority Data

Jul. 31, 2012 (JP) .................................. 2012-170366
Jul. 31, 2012 (JP) .................................. 2012-170367

(51) Int. Cl.
*G01N 29/44* (2006.01)
*G01N 29/24* (2006.01)
*G01N 29/11* (2006.01)

(52) U.S. Cl.
CPC .............. *G01N 29/11* (2013.01); *G01N 29/24* (2013.01); *G01N 29/2487* (2013.01);
(Continued)

(58) Field of Classification Search
CPC .............. G01N 29/11; G01N 29/2487; G01N 29/4436; G01N 29/24; G01N 2291/267; G01N 2291/044
(Continued)

(56) References Cited

U.S. PATENT DOCUMENTS 4,785,667 A * 11/1988 Miyajima .......... G01N 29/0645
73/618
5,005,420 A 4/1991 Miyajima
(Continued)

FOREIGN PATENT DOCUMENTS

EP 0317629 A1 5/1989
JP 10-221309 A 8/1998
(Continued)

OTHER PUBLICATIONS

International Searching Authority, International Search Report (ISR) and Written Opinion for International Application No. PCT/JP2013/004637, Nov. 5, 2013, 8 pages, Japan Patent Office, Japan.
European Patent Office, Extended European Search Report for Application No. 13826436.1, Jun. 10, 2015, 6 pages, Germany.

*Primary Examiner* — J M Saint Surin
(74) *Attorney, Agent, or Firm* — Alston & Bird LLP

(57) ABSTRACT

A method for measuring the degree of fusion involves: a step for creating a dividing pulse amplitude curve by using a probe that emits ultrasound beams; a step for scanning the probe that emits ultrasound beams at a predetermined angle
(Continued)

on a surface that has weld beads of multiple welding specimens having different degrees of fusion and for obtaining beam path length information from the dividing pulse amplitude curve and the height of an F echo that returned to the probe after hitting the fused section of a welding site; and a step for obtaining a regression formula expressing the relationship between the beam path length information and the degree of fusion.

21 Claims, 11 Drawing Sheets

(52) U.S. Cl.
CPC ..... *G01N 29/4409* (2013.01); *G01N 29/4436* (2013.01); *G01N 2291/044* (2013.01); *G01N 2291/267* (2013.01)

(58) Field of Classification Search
USPC .................................................. 73/600, 599
See application file for complete search history.

(56) References Cited

U.S. PATENT DOCUMENTS

| | | | | |
|---|---|---|---|---|
| 7,204,147 | B2* | 4/2007 | Fujimoto | G01N 29/11 73/598 |
| 7,712,369 | B2* | 5/2010 | Georgeson | G01N 29/04 73/602 |
| 7,757,558 | B2* | 7/2010 | Bossi | G01N 29/11 73/609 |
| 7,779,694 | B2* | 8/2010 | Iizuka | G01N 29/07 73/622 |
| 7,900,516 | B2* | 3/2011 | Fukutomi | G01N 29/069 73/598 |
| 8,051,717 | B2* | 11/2011 | Fukutomi | G01N 29/069 73/598 |
| 2006/0191343 | A1 | 8/2006 | Fujimoto et al. | |

FOREIGN PATENT DOCUMENTS

| | | |
|---|---|---|
| JP | 2004-333387 A | 11/2004 |
| JP | 2007-178197 A | 7/2007 |
| JP | 2008-209231 A | 9/2008 |
| JP | 2009-180646 A | 8/2009 |
| JP | 2010-043989 A | 2/2010 |
| WO | WO 88/09931 A1 | 12/1988 |

* cited by examiner (a)

(b)

(a)

(b)

TRACE WIDTH=W2−W1
W1,W2:BEAM PATH LENGTH (mm)

(a)

(b)

(a)

(b)

(a)

(b)

METHOD FOR MEASURING HEIGHT OF LACK OF PENETRATION AND ULTRASONIC FLAW DETECTOR

CROSS REFERENCE TO RELATED APPLICATIONS

This application is a national stage application, filed under 35 U.S.C. §371, of International Application No. PCT/JP2013/004637, filed Jul. 31, 2013, which claims priority to Japanese Application No. 2012-170366, filed Jul. 31, 2012 and Japanese Application No. 2012-170367, filed Jul. 31, 2012, the contents of which being hereby incorporated by reference in their entirety.

BACKGROUND

Technical Field

The technique disclosed in this specification relates to methods for measuring the depth of partial penetration of a weld (i.e., methods for measuring the height of lack of penetration), and ultrasonic flaw detectors used in this method.

Description of Related Art

Steel bridges include a steel plate floor for directly supporting a live load. The steel plate floor includes a deck plate, a longitudinal rib, and a cross rib. The longitudinal rib and the cross rib are welded to a back surface of the deck plate. Fatigue cracks might be formed from a weld of such a welded structure due to a long term use. Thus, to secure an adequate fatigue resistance, the specifications for highway bridges provide that the depth of partial penetration of a weld between a deck plate and a U-shaped rib that is widely used as a longitudinal rib and has a U-shaped cross section is 75% or more of the thickness of the rib.

Ultrasonic testing, one of methods of nondestructive testing, is often conducted to test a welding quality on a steel plate floor etc. However, the technique for directly measuring the depth of partial penetration of the weld has not been fully developed.

Conventionally, a welding test has been conducted in advance to determine welding conditions that can ensure the depth of partial penetration satisfying the criterion. Then, the criterion of the depth of partial penetration has been assured by reproducing the welding conditions.

CITATION LIST

Patent Document

PATENT DOCUMENT 1: Japanese Unexamined Patent Publication No. 2009-180646
PATENT DOCUMENT 2: Japanese Unexamined Patent Publication No. 2004-333387
PATENT DOCUMENT 3: Japanese Unexamined Patent Publication No. 2007-178197

BRIEF SUMMARY

However, in the method where the welding conditions determined in advance are reproduced, the depth of partial penetration can be assured only by checking a welding record. Thus, it is difficult to obtain adequate reliability.

In view of the foregoing, it is an object of the present invention to provide a method for measuring the depth of partial penetration of a weld (i.e., a method for measuring the height of lack of penetration) to ensure adequate reliability of a product produced by welding.

One embodiment of the present disclosure is directed to a method for measuring the height of lack of penetration in a weld if a first member is welded to a second member. The method for measuring a height of lack of penetration in a weld, the method comprising steps of: using a probe applying an ultrasonic beam to an object to define a dividing curve of an echo height as a reference level for evaluating a height of an F echo that is reflected by a part of lack of penetration of the weld and returned to the probe; obtaining beam path length information based on the dividing curve of the echo height and the height of the F echo obtained by moving the probe that applies the ultrasonic beam to the object at a predetermined angle to scan surfaces of a plurality of weld test samples having different heights of lack of penetration, a weld bead being disposed on the surface; and formulating a regression equation showing a relation between the beam path length information and the height of lack of penetration.

The reference level for evaluating the height of the F echo in the measurement method is selected from, e.g., the dividing curves of echo heights provided in JIS Z 3060 "Method for Ultrasonic Examination for Welds of Ferritic Steel." Specifically, the reference level is a selected one of an L/2 line, an L line, an M line, or an H line. In the step of obtaining the beam path length information in this measurement method, the probe is disposed on the weld test sample so that the ultrasonic beam is directed toward a weld line of the weld test sample at a right angle. Then, the probe is moved forward or backward along the ultrasonic beam direction to scan the weld test sample. Then, the beam path length information is obtained based on the dividing curve of echo height and the height of the F echo applied from the probe to the weld line at a predetermined refraction angle, reflected by a part of lack of penetration of a weld, and returned to the probe.

Here, when the probe is moved in a direction away from a position of a weld bead to scan the weld test sample, the height of the F echo decreases around 0.5 skip distance, and increases around 1.5 skip distance. Thus, examples of the measurement method include a method in which the beam path length where, e.g., the F echo decreases to the reference level below 0.5 skip distance is used as the beam path length information (i.e., a beam path length method), and a method in which a beam path length range (a trace width) corresponding to a range where the F echo exceeds the reference level around 1.5 skip distance may be used as the beam path length information (i.e., a trace width method). The regression equation is formulated based on a relation between the height of lack of penetration and the beam path length or the trace width obtained as above.

The measurement method of the embodiment of the present disclosure may further include steps of: placing the probe applying the ultrasonic beam to the weld line between the first member and the second member; obtaining the beam path length information by measuring the height of the F echo applied from the probe to the weld line at a predetermined refraction angle, reflected by the part of lack of penetration, and returned to the probe; and applying the beam path length information to the regression equation to calculate the height of lack of penetration. The depth of partial penetration is determined by subtracting the calculated height of lack of penetration from the thickness of the first member.

This method allows calculation of the height of lack of penetration in the weld based on the measurement of a welded product and determination of the depth of partial penetration. This enables determination of whether each product is passed or failed. Thus, highly reliable products can be released, and bridges in which fatigue cracks are unlikely to be formed can be constructed.

An ultrasonic flaw detector of one embodiment of the present disclosure includes a probe, a flaw detection unit, an AD conversion unit, a signal storage unit, a memory, and an unit for calculating height of lack of penetration. The probe is configured to apply the ultrasound to an object. The flaw detection unit is configured to control operation of the probe, and to measure a beam path length and the height of an F echo of the ultrasound reflected by a part of lack of penetration of the object, and returned to the probe. The AD conversion unit is configured to convert a value measured by the flaw detection unit to a digital value. The signal storage unit is configured to store the measured value converted by the AD conversion unit. The memory is configured to store data about a dividing curve of an echo height and the data about a regression equation showing a relation between the beam path length information and the height of lack of penetration. The unit for calculating height of lack of penetration is configured to calculate the height of lack of penetration in a weld between a first member and a second member that form the object, based on the measured value stored in the signal storage unit and the data stored in the memory.

The unit for calculating height of lack of penetration may determine, as the beam path length information, a trace width that is a beam path length range where the height of the F echo returned to the probe on the first member exceeds the dividing curve of the echo height, and apply the trace width to the regression equation to calculate the height of lack of penetration.

Alternatively, the unit for calculating height of lack of penetration may determine, as the beam path length information, a beam path length where the height of the F echo returned to the probe on the first member corresponds to the dividing curve of the echo height, and apply the beam path length to the regression equation to calculate the height of lack of penetration.

Such an ultrasonic flaw detector enables automatic calculation of the height of lack of penetration, and thus reduces human errors. Even if an operator is unskilled in the measurement operation, the beam path length information and the height of lack of penetration can be automatically calculated based on the measurements.

The ultrasonic flaw detector may further includes a determining unit configured to determine that the weld is failed if the height of lack of penetration calculated by the unit for calculating height of lack of penetration exceeds a predetermined reference value, and determine that the weld is passed if the height of lack of penetration is less than or equal to the reference value.

The method for measuring the height of lack of penetration in a weld according to one embodiment of the present disclosure can provide adequately high reliability of a product produced by welding.

DETAILED DESCRIPTION OF VARIOUS EMBODIMENTS

Figure 1:
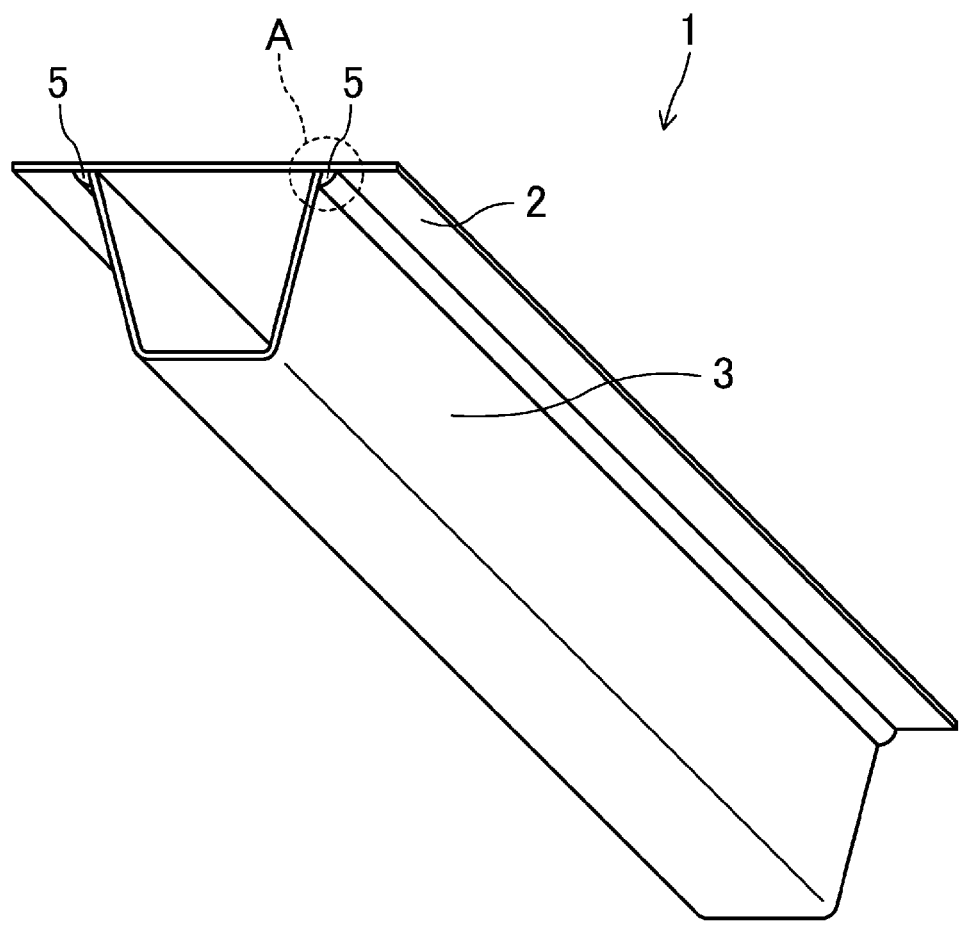
FIG. 1(a) is a perspective view of a steel plate floor of a bridge.
FIG. 1(b) is an enlarged side view of a weld between a U-shaped rib and a deck plate.
Figure 1:
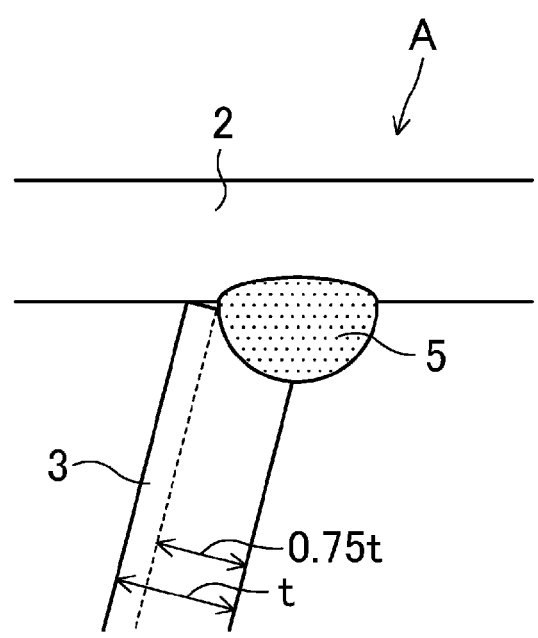

FIG. 1(a) is a perspective view of a steel plate floor of a bridge. FIG. 1(b) is an enlarged side view of a weld between a U-shaped rib and a deck plate (a region A in FIG. 1(a)).

FIG. 1(a) illustrates a steel plate floor 1 including a flat deck plate (a second member) 2 and a U-shaped rib (a first member) 3. The U-shaped rib 3 is welded to a back surface of the deck plate 2 and has a U-shaped cross section. FIG. 1(b) illustrates that a weld bead 5 having a predetermined depth of partial penetration is formed on a weld between the U-shaped rib 3 and the deck plate 2. In other words, the weld has a predetermined height of lack of penetration.

The steel plate floor 1 is a target object to be measured in a method for measuring the depth of partial penetration of a weld according to one embodiment of the present disclosure.

The inventors of the present application studied various methods for precisely measuring the depth of partial penetration of a weld. FIG. 2(b) is a graph showing dividing curves of echo heights obtained from a test piece illustrated in FIG. 2(a). FIG. 3 is a graph showing the dividing curves of echo heights and a trace (a broken line in the graph) of an F echo returned to a probe.

Here, Patent Document 1 discloses a method in which the height of an F echo relative to dividing curves of echo heights is determined, a determination curve is created by using a relation between the relative height of the echo and the height of a part of lack of penetration of a weld of a test piece (i.e., the height of lack of penetration), and the height of lack of penetration in the target object is determined by using the determination curve.

Patent Document 2 discloses a method in which master data is created by measuring an F echo at a position determined based on the thickness of a U-shaped rib, an incidence angle of a pulse, etc., and the height of lack of penetration is calculated by applying an F echo of the target object observed at the position to the master data.

In addition, it is conceivable to determine the height of lack of penetration in a target object based on an index, which is the ratio between an F echo and an echo (a so-called B echo) reflected by a back surface of the U-shaped rib 3 (see FIGS. 1(a) and 1(b)) opposite to a surface thereof being in contact with a probe, with the position of the probe fixed.

If the probe scans the U-shaped rib illustrated in FIGS. 1(a) and 1(b) in a direction away from a position where the prove is in contact with the weld bead, and applies the ultrasound to a part of lack of penetration of a weld at a predetermined refraction angle, an F echo returned from the part of lack of penetration to the probe is observed. As shown in FIG. 3, this F echo temporarily decreases around 0.5 skip distance, and increases again around 1.5 skip distance.

For example, in the methods of Patent Documents 1 and 2, it is necessary to fix a probe at a position that allows the height of an F echo to be high. Thus, the distance from the probe to the weld is less than 0.5 skip distance (see the broken line in FIG. 3). However, if the U-shaped rib has a thickness as small as approximately 6 mm, the probe may be in contact with the weld so that it is difficult to obtain precise measurements.

In the method where the ratio between a B echo and an F echo is used, the amplitude of a measured B echo is larger than that of a measured F echo, and thus the measured B echo is unstable. This may lead to a larger error.

In view of the above difficulties, the inventors of the present application further studied a simple method for precise measurement. As a result, they found that the range of beam path lengths in which the height of an F echo corresponds to a predetermined dividing curve of echo height, or the range of beam path lengths in which the height of an F echo exceeds the predetermined dividing curve of echo heights has a good relation with the height of lack of penetration in a weld.

The inventors defined the beam path length and the range of the beam path lengths as beam path length information. The inventors used a probe to scan a surface of one of a plurality of weld test samples each having different heights of lack of penetration. A weld bead is disposed on this surface. The probe applies ultrasonic beams to the surface at a predetermined angle. Then, the inventors determined the beam path length information based on an F echo reflected by a part of lack of penetration of the weld and returned to the probe. Then, the inventors obtained a regression equation based on a relation between the beam path length information and the height of lack of penetration. The inventors arrived at and confirmed in practice a simple method in which the height of lack of penetration can be precisely measured by applying the beam path length information of a measured F echo of a target object to the regression equation. Specific embodiments of the present invention will be described below.

(First Embodiment)

The beam path length information, which shows, for example, the "trace width," will be described in detail below. In this specification, the "trace width" means the range of beam path lengths in which the height of an F echo exceeds a predetermined echo-dividing curve serving as a reference level (e.g., W2-W1 in FIG. 3). The inventors of the present application confirmed that the height of lack of penetration can be determined by measuring an object with the ultrasound, determining the "trace width" from the measurement, and then applying the "trace width" to a regression equation formulated in advance.

—Steps of Measurement Method—

<Generation of Dividing Curves of Echo Heights>

In the measurement method of this embodiment, an ultrasonic test is conducted along the following steps, and the dividing curves of echo heights are obtained before the measurement of an object. The measurement method of this embodiment complies with JIS Z 3060 (2002) "Method for Ultrasonic Examination for Welds of Ferritic Steel."

An ultrasonic flaw detector complying with JIS Z 2352 is used. A probe B5K10×10A70 is used as an example probe. This probe includes a transducer having dimensions of 10 mm×10 mm. The frequency of the ultrasound applied from the probe to a standard test piece is 5 MHz. The refraction angle of the ultrasound is 70°.

A test piece STB-A1 is used as a standard test piece. A test piece RB-41 No. 1 is used as a comparison test piece. Glycerin paste or water is used as a coupling medium applied between each test piece and the probe.

First, the probe index and the refraction angle are measured, and the time base is adjusted, by using the standard test piece, STB-A1.

Next, probes are disposed in turn at positions (1)-(6) on an upper surface and a back surface of the test piece RB-41 No. 1 as illustrated in FIG. 2(a). Then, the ultrasound is applied to the test piece RB-41 No. 1 at a predetermined refraction angle (70° in this embodiment) so that the echo height is measured in a predetermined reference hole. Here, the maximum echo heights measured in the reference hole are plotted relative to the beam path length to form an H line, which is a reference working sensitivity. An M line indicates values lower by 6 dB than the H line does. An L line indicates values lower by 6 dB than the M line does. An L/2 line indicates values lower by 6 dB than the L line does. In this manner, the dividing curves of echo heights in FIG. 2(b) are obtained.

<Formulation of Regression Equation>

Figure 4:
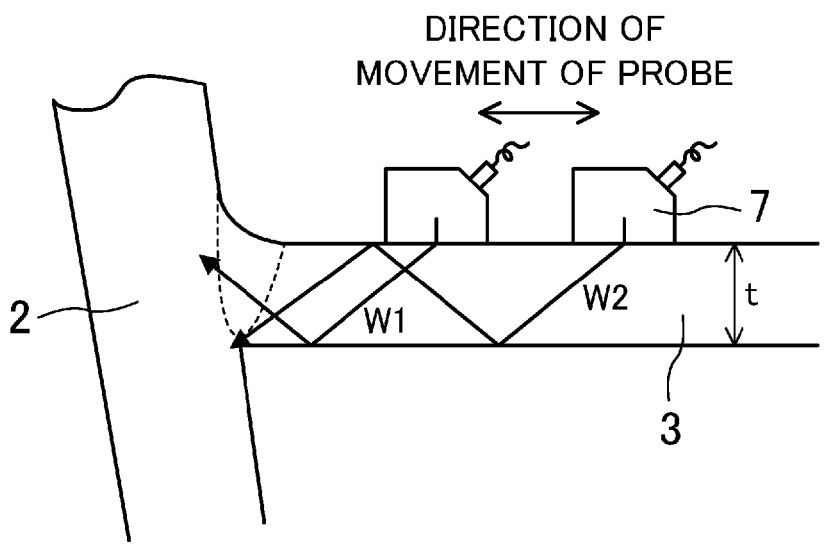
FIG. 4(a) illustrates how a probe is moved forward or backward to scan a U-shaped rib having a thickness of 6 mm.
FIG. 4(b) is a graph showing the trace width based on a measurement of an object.
Figure 4:
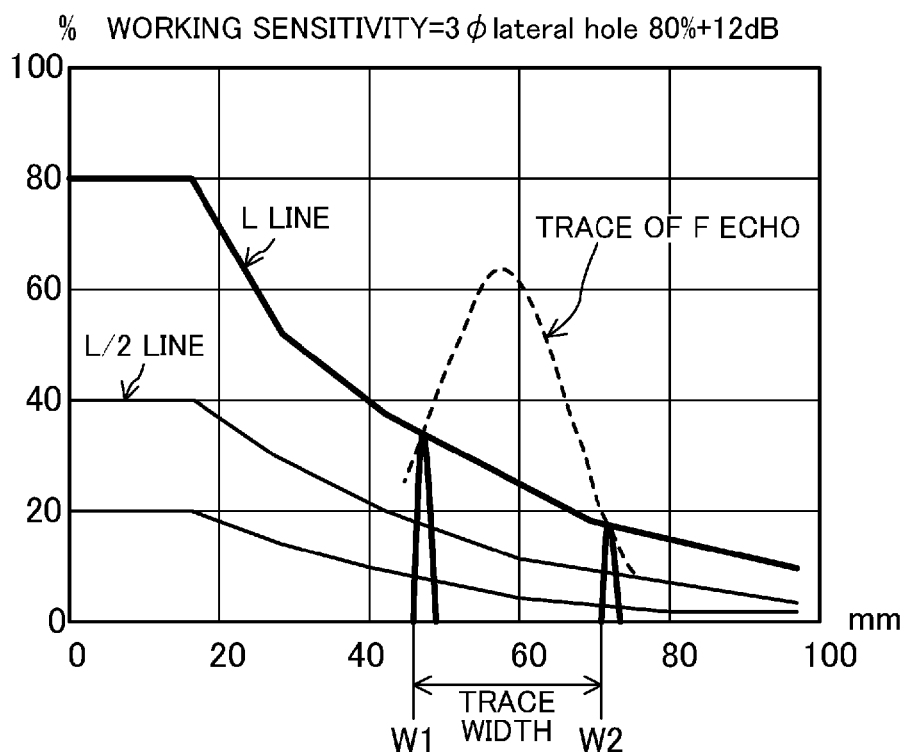

A plurality of weld test samples are measured with the ultrasound by using a probe 7 moved, e.g., forward or backward to scan a U-shaped rib 3 so that an ultrasonic beam is directed toward a weld line at a predetermined angle (e.g., a right angle). The plurality of weld test samples each include the U-shaped rib 3 and a deck plate 2 as illustrated in FIG. 4(a), and have different heights of lack of penetration. The U-shaped rib 3 has the same thickness as a target U-shaped rib does, i.e., a thickness of 6 mm. Here, the height of an F echo that is applied from the probe 7 to the weld line at a predetermined refraction angle (e.g., 70°), reflected by a part of lack of penetration of a weld, and returned to the probe 7 is measured.

As shown in FIG. 4(b), the trace width is determined with dividing curves of echo heights and a measurement of the F echo. Then, a regression equation is formulated based on a relation between the trace width and the height of lack of penetration. In the example in FIG. 4(b), the L line of the dividing curves of echo heights is used as a reference level for evaluation of the height of the F echo. The reference level is not limited to the L line, and any reference level may be determined as long as the reference level enables precise estimation of the height of lack of penetration.

Figure 5:
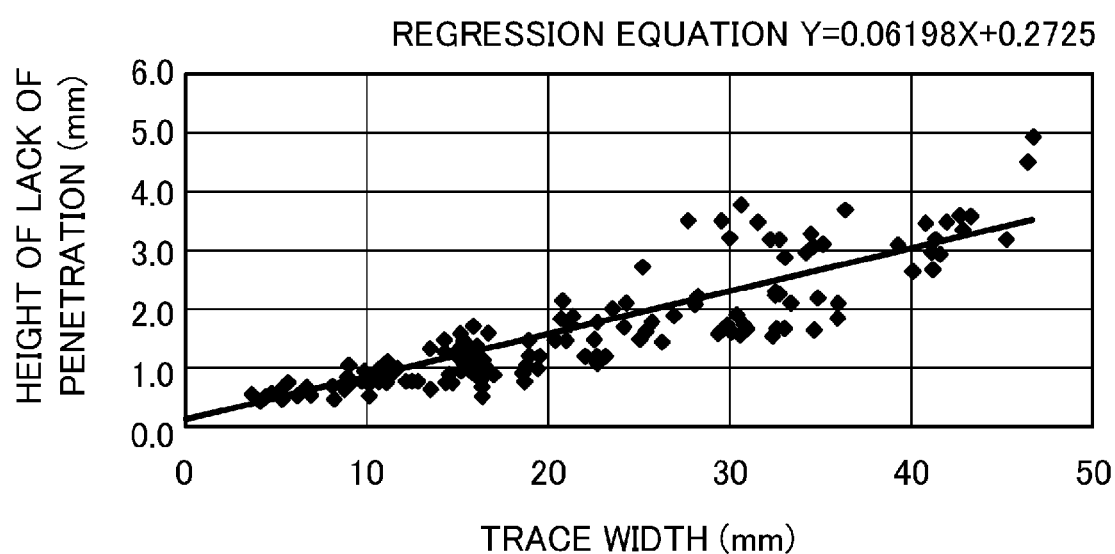
FIG. 5 is a graph showing an example regression equation showing a relation between the height of lack of penetration (mm) and the trace width (mm) obtained when the U-shaped rib has a thickness of 6 mm and an L line of the dividing curves of echo heights is used as a reference level.

FIG. 5 is a graph showing an example regression equation showing a relation between the height of lack of penetration (mm) and the trace width (mm), where the U-shaped rib has a thickness of 6 mm. This regression equation can be obtained by plotting the measurements and using, e.g., the least square method.

<Measurement of Height of Lack of Penetration/Pass-Fail Determination>

Next, as illustrated in FIG. 4(a), to scan the U-shaped rib 3 of the target steel plate floor 1 to be measured, the probe 7 is moved forward or backward so that an ultrasonic beam is directed toward a weld line at a right angle. Then, the height of an F echo applied from the probe 7 to the weld line at a predetermined refraction angle, reflected by a part of lack of penetration, and returned to the probe is measured.

Next, the trace width is determined from the measured height of the F echo where the L line of the dividing curves of echo heights in FIG. 3 serves as a reference level. Subsequently, the height of lack of penetration in the weld of the steel plate floor 1 can be calculated by applying the trace width obtained as above to the regression equation shown in FIG. 5. If the regression equation is Y=0.06198X+0.2725, the height of lack of penetration can be calculated as approximately 1.51 mm, where the trace width is, e.g., 20 mm.

Finally, it is determined whether the calculated height of lack of penetration satisfies a predetermined criterion. According to the specifications for highway bridges, the criterion of the depth of partial penetration of the target steel plate floor 1 is 75% or more of the thickness of the U-shaped rib. If the U-shaped rib 3 is 6 mm in thickness, the steel plate floor 1 having a weld in which the height of lack of penetration is 1.5 mm or less is determined to be passed, and the steel plate floor 1 having a weld in which the height of lack of penetration is more than 1.5 mm is determined to be failed.

The target object to be measured in the measurement method of this embodiment is not limited to the steel plate floor. Any structure created by welding is applicable.

—Advantages of Measurement Method—

The measurement method of this embodiment allows calculation of the height of lack of penetration in a weld based on the measurement of an actually welded product, and enables pass/fail determination of the depth of partial penetration of every product. Thus, highly reliable products can be released, and bridges in which fatigue cracks are unlikely to be formed can be constructed. For example, the dividing curves of echo heights and the regression equation used for the measurement, and the measurements of the target steel plate floor 1 to be measured are stored as data, which can be used to review the test results.

The shape of a penetrating portion of a weld root varies. For this reason, in the methods of Patent Documents 1 and 2 where the measurement is conducted with the probe 7 disposed at a fixed position, a reflection echo having a proper height might not be obtained. In contrast, in the method of this embodiment, the probe 7 is moved forward or backward to scan the U-shaped rib 3 (the first member) for measurement, and thus the height of lack of penetration can be precisely calculated.

In the methods of Patent Documents 1 and 2, the evaluation is made based on the echo height. If the U-shaped rib 3 is thin, the probe 7 is in contact with the weld, and thus might not work. In contrast, in the measurement method of this embodiment, an F echo can be measured at a position away from the weld to calculate the height of lack of penetration, as compared with the method in which the ultrasound is directly applied to a weld. Thus, even if the U-shaped rib is 6 mm or less in thickness, the trace width can be determined, and the height of lack of penetration can be calculated. The measurement with the method of this embodiment has showed that even if the U-shaped rib 3 is 6 mm in thickness, the measurement error of the height of lack of penetration can fall within approximately ±0.5 mm. That is, the method of this embodiment allows the measurement with higher precision than the typical methods do.

In the measurement method of this embodiment, the height of lack of penetration can be measured without a B echo of which the measured value is unstable. Thus, the method of this embodiment enables the measurement with higher precision than the methods in which the ratio between a B echo and an F echo is used do.

As described above, the measurement method of this embodiment complies with JIS Z 3060 (2002) "Method for Ultrasonic Examination for Welds of Ferritic Steel." In the measurement method of this embodiment, the devices and standard test pieces provided in JIS can be used without special facilities. The measurement might be made with a dedicated ultrasonic flaw detector that stores programs etc. for implementing the method. Alternatively, the measurement may be made with a general ultrasonic flaw detector, and a personal computer etc. may be used to store signals and undergo processes, such as imaging of the measurement. The trace width and the height of lack of penetration may be calculated not with an ultrasonic flaw detector but in a manual way.

—Example of Modification to Thickness of U-Shaped Rib—

The measurement method of the embodiment where the U-shaped rib 3 welded to the deck plate 2 is 6 mm in thickness has been described. Even if the U-shaped rib 3 has a modified thickness, the depth of partial penetration of a weld can be measured under a similar method. Measurement steps where the U-shaped rib 3 is 8 mm in thickness will be described below.

First, the dividing curves of echo heights shown in FIG. 3 are obtained according to a similar method in which the test pieces and devices used for the U-shaped rib 3 that is 6 mm in thickness are used.

Next, a plurality of weld test samples are measured with the ultrasound by using a probe 7 moved forward or backward to scan a U-shaped rib 3 so that an ultrasonic beam is directed toward a weld line at a predetermined angle (e.g., a right angle). The plurality of weld test samples each include the U-shaped rib 3 and a deck plate 2 as illustrated in FIG. 6(a), and have different heights of lack of penetration. Here, the height of an F echo that is applied from the probe 7 to the weld line at a predetermined refraction angle (e.g., 70°), reflected by a part of lack of penetration of a weld, and returned to the probe 7 is measured.

Here, in moving the probe 7 forward or backward for scanning, the flaw detection skip distances can include 1.5, 2.5, and 3.5. As described above, it is most preferable to move the probe 7 for scanning around a position at which the flaw detection skip distance is 1.5.

Figure 6:
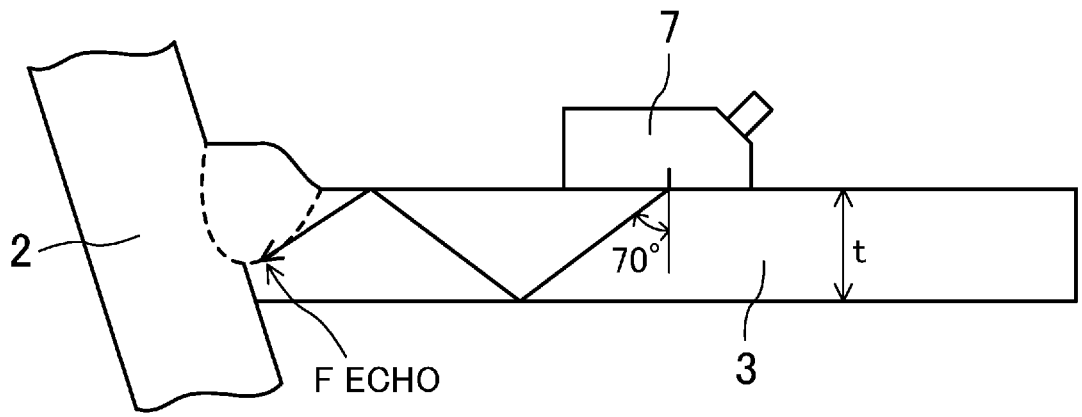
FIG. 6(a) illustrates how a probe is moved forward or backward to scan a U-shaped rib having a thickness of 8 mm.
FIG. 6(b) is a graph showing the trace width based on a measurement of an object.
Figure 6:
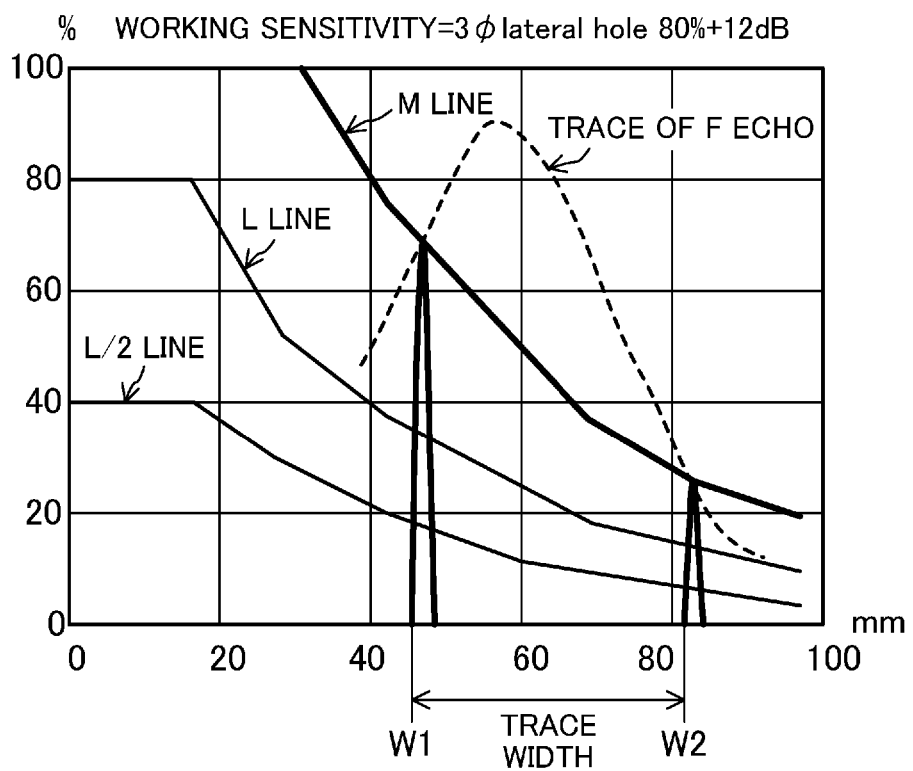

As shown in FIG. 6(*b*), the trace width is determined with the dividing curves of echo heights and a measurement of an F echo. Then, a regression equation is formulated based on a relation between the trace width and the height of lack of penetration. Here, the M line of the dividing curves of echo heights is used as a reference level for determining the trace width. The reference level is not limited to the M line, and any reference level may be determined as long as the reference level enables precise estimation of the height of lack of penetration.

Figure 7:
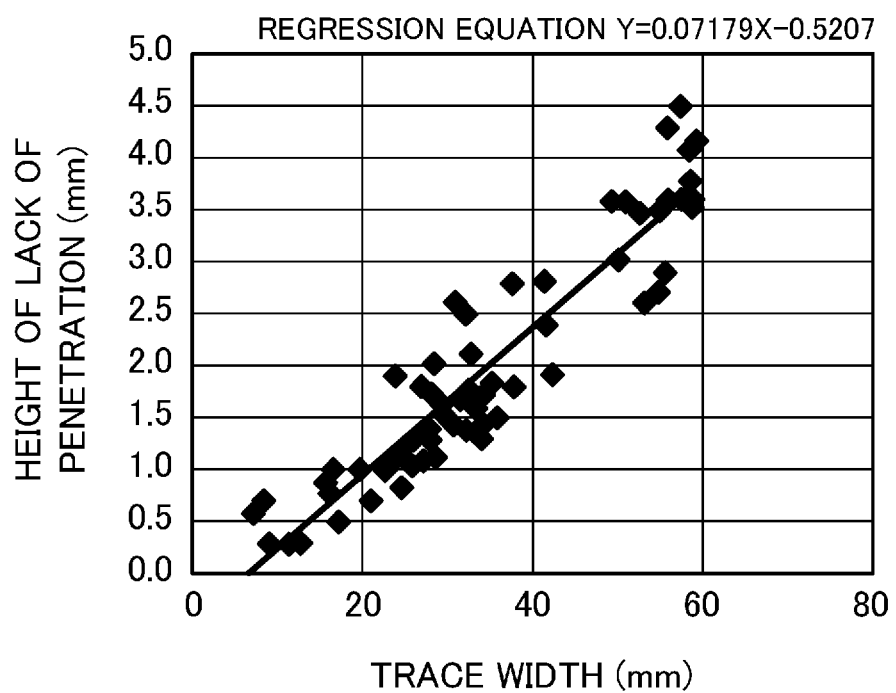
FIG. 7 is a graph showing an example regression equation showing a relation between the height of lack of penetration (mm) and the trace width (mm) obtained when the U-shaped rib has a thickness of 8 mm and an M line of the dividing curves of echo heights is used as a reference level.

FIG. 7 is a graph showing an example regression equation showing a relation between the height of lack of penetration (mm) and the trace width (mm), where the U-shaped rib has a thickness of 8 mm.

Next, as illustrated in FIG. 6(*a*), to scan the U-shaped rib 3 of the target steel plate floor 1 to be measured, the probe 7 is moved forward or backward so that an ultrasonic beam is directed toward a weld line at a right angle. Then, the height of an F echo applied from the probe 7 to the weld line at a predetermined refraction angle, reflected by a part of lack of penetration, and returned to the probe is measured.

Next, the trace width is determined from the measured height of the F echo where the M line of the dividing curves of echo heights in FIG. 3(*b*) serves as a reference level. Subsequently, the height of lack of penetration in the weld of the steel plate floor 1 can be calculated by applying the trace width obtained as above to the regression equation shown in FIG. 7.

Finally, it is determined whether the calculated height of lack of penetration satisfies a predetermined criterion. According to the specifications for highway bridges, if the U-shaped rib 3 of the target steel plate floor 1 is 8 mm in thickness, the steel plate floor 1 having a weld in which the height of lack of penetration is 2.0 mm is determined to be passed, and the steel plate floor 1 having a weld in which the height of lack of penetration is more than 2.0 mm is determined to be failed. Any criterion for pass/fail determination may be determined depending on a target object to be measured.

As described above, the measurement method of this embodiment enables precise measurement of the height of lack of penetration and the depth of partial penetration even if the U-shaped rib 3 is 8 mm in thickness. In this manner, the thickness of the U-shaped rib 3 is not limited to a particular thickness in the measurement method of this embodiment. The method of this embodiment can be used by determining a regression equation corresponding to the thickness of the U-shaped rib 3 as long as the thickness of the U-shaped rib 3 is within the range in which the reflection echo having an adequate height can be observed.

—Ultrasonic Flaw Detector—

Figure 8:
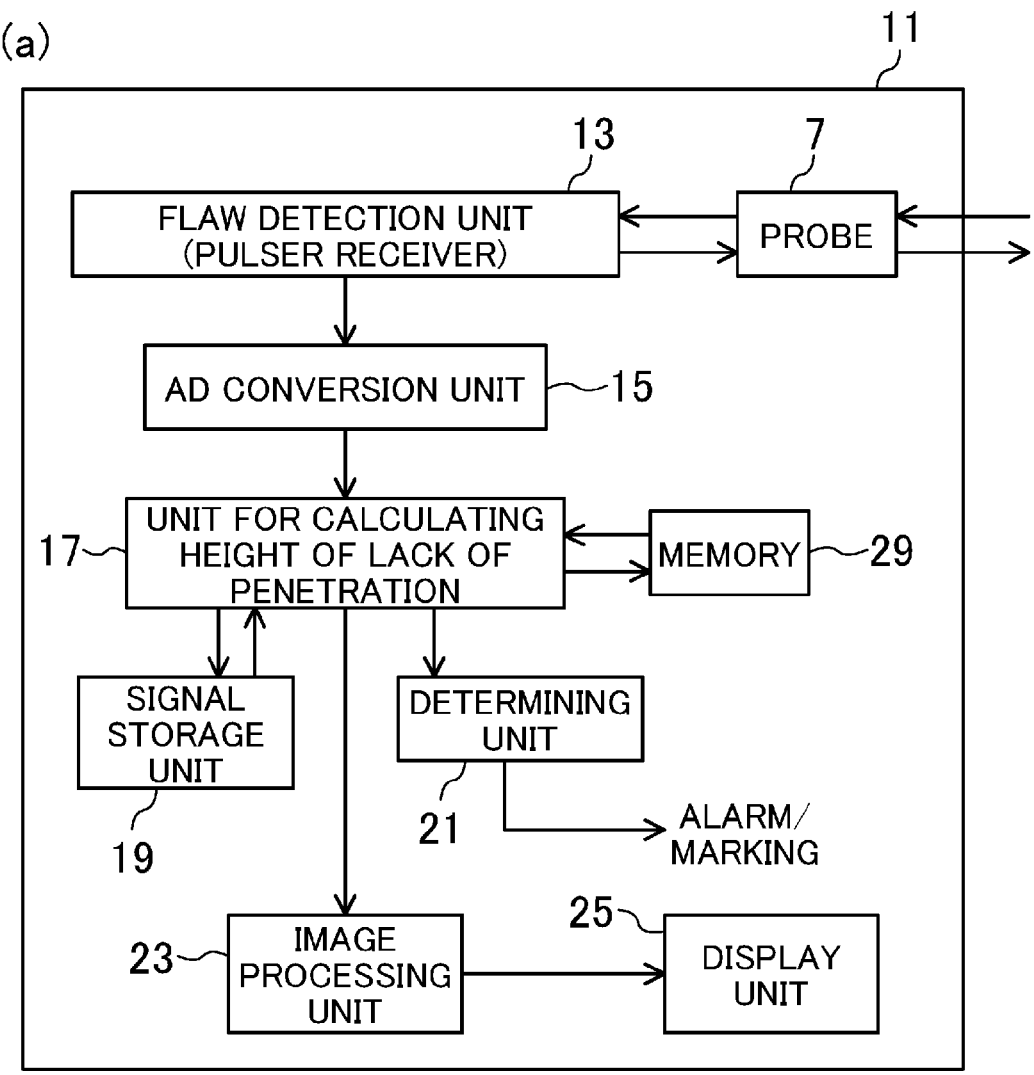
FIG. 8(a) is a block diagram of an example ultrasonic flaw detector used for a measurement method for the depth of partial penetration of a weld according to the embodiment of the present disclosure.
FIG. 8(b) is a graph showing example measurements, which are displayed by a display unit, at a plurality of measurement points.
Figure 8:
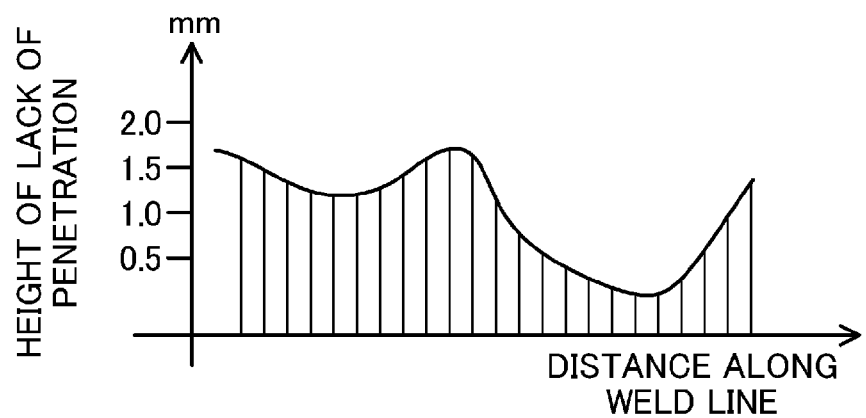

FIG. 8(*a*) is a block diagram of an example ultrasonic flaw detector used in the method for measuring the depth of partial penetration of the weld according to the embodiment of the present disclosure.

As shown in the figure, the ultrasonic flaw detector 11 of this embodiment includes the probe 7, a flaw detection unit (a pulser receiver) 13, an AD conversion unit 15, a signal storage unit 19, a memory 29, an unit for calculating height of lack of penetration 17, and a determining unit 21. The probe 7 applies the ultrasound to an object. The flaw detection unit 13 controls operation of the probe 7, and measures the beam path length and the height of an F echo of the ultrasound reflected in the object and returned to the probe 7. The AD conversion unit 15 converts a value measured by the flaw detection unit 13 to a digital value. The signal storage unit 19 stores the measured value converted by the AD conversion unit 15. The memory 29 stores data about the dividing curves of echo heights, and data about a regression equation showing the relation between the beam path length information and the height of lack of penetration. Based on the measured values stored in the signal storage unit 19 and the data stored in the memory 29, the unit for calculating height of lack of penetration 17 calculates the beam path length information such as the trace width, and the height of lack of penetration in the weld between the target U-shaped rib (the first member) to be measured and the deck plate (the second member). The determining unit 21 determines whether the weld is passed or failed based on the height of lack of penetration calculated by the unit for calculating height of lack of penetration 17.

The ultrasonic flaw detector 11 may further include an image processing unit 23 and a display unit 25. The image processing unit 23 performs image processing on the data about the height of lack of penetration calculated by the unit for calculating height of lack of penetration 17. The display unit 25 displays the data about the height of lack of penetration on which the image processing has been performed.

The probe 7 is disposed on a predetermined surface of a target object with glycerin or water interposed therebetween. In the above-described measurement method, the measurement is made at a refraction angle of 70°. The probe 7 may be a part of the ultrasonic flaw detector 11, or may be connected, as an independent member, with the ultrasonic flaw detector 11.

The signal storage unit 19 is, e.g., a publicly known memory. In the above-described measurement method, the signal storage unit 19 stores digitized values etc. of a target object. The memory 29 stores data about each dividing curve of echo heights. The memory 29 also stores, for example, data about the beam path length information such as the trace width of a target object to be tested or measured, data about the regression equation obtained from the beam path length information such as the trace width, and data about the height of lack of penetration calculated by the unit for calculating height of lack of penetration 17. These data are stored as the data obtained at the measurement positions arranged along the longitudinal direction of the target object.

The unit for calculating height of lack of penetration 17 determines, as the beam path length information (the trace width in this embodiment), the range of the beam path length in which the height of an F echo that is applied to a weld line between the first member (the U-shaped rib) and the second member (the deck plate) at a predetermined refraction angle, reflected by a part of lack of penetration of a weld, and returned to the probe 7 exceeds a dividing curve of echo height serving as a reference level when the probe 7 is moved forward or backward to scan an object so that an ultrasonic beam is directed toward the weld line at a right angle.

Next, to calculate the height of lack of penetration, the unit for calculating height of lack of penetration 17 applies the trace width to the regression equation formulated in advance based on the relation between the trace width and the height of lack of penetration. A program for automatically performing these calculations may be stored in advance in a memory etc. (another memory different from the memory 29) of the ultrasonic flaw detector 11. Alternatively, the hardware may be configured to allow the unit for calculating height of lack of penetration 17 to perform the calculations.

The determining unit 21 determines that the weld is failed if a measured value calculated by the unit for calculating height of lack of penetration 17 exceeds a reference value determined in advance depending on the target object. Then, the determining unit 21 outputs, e.g., a signal indicating that the weld is failed. The determining unit 21 also determines that the weld is passed if the measured value is less than or equal to the predetermined reference value. Then, the determining unit 21 outputs, e.g., a signal indicating that the weld is passed. The ultrasonic flaw detector 11 may be configured to sound an alarm if the weld is determined to be failed, or to mark the failed target object. The ultrasonic flaw detector 11 may be configured to perform processes until the calculation of the height of lack of penetration without providing the determining unit 21.

The height of lack of penetration in the target object (the U-shaped rib in this embodiment) is measured along the longitudinal direction (i.e., the extension direction of the weld line) of the target object at predetermined intervals, and the data about the measurements are stored in the signal storage unit 19. In this case, the image processing unit 23 produces a graph representing the calculated height of lack of penetration and the positional information (information about the location at which the measurement was made along the extension direction of the weld line). Specifically, the image processing unit 23 outputs image data showing the height of lack of penetration calculated at the plurality of measurement points arranged along the extension direction of the weld line. The image data are provided for each of the plurality of measurement points. Based on the image data, the display unit 25 displays the height of lack of penetration for each of the points arranged along the weld line in a visually recognizable manner.

FIG. 8(*b*) is a graph showing example measurements, which are displayed by the display unit 25, at a plurality of measurement points. The display of the measurements of the height of lack of penetration eases understanding of the measurements. The display unit 25 may not always be provided in the ultrasonic flaw detector 11. The measurements may be displayed on a screen of a computer etc. connected with the ultrasonic flaw detector 11.

The ultrasonic flaw detector 11 of this embodiment enables automatic calculation of the height of lack of penetration, thus reducing human errors. Even if an operator is unskilled in the measurement operation, the trace width and the height of lack of penetration can be automatically calculated based on the measurements, and the depth of partial penetration can be examined.

(Second Embodiment)

In a method for measuring the depth of partial penetration of a weld part according to a second embodiment of the present invention, a steel plate floor 1 in FIG. 1(*a*) is measured in a manner similar to that in the method of the first embodiment. The inventors of the present application further studied a method for precisely measuring the depth of partial penetration of a weld. Then, the inventors of the present application found the correlation between the height of lack of penetration in a weld and the beam path length W (see FIGS. 2 and 9(*b*)) where the height of an F echo of the ultrasound applied to the weld at a predetermined reflection angle corresponds to a predetermined echo-dividing curve. Specifically, the inventors of the present application found that the height of lack of penetration increases as the beam path length W increases.

The inventors of the present application further conducted studies and arrived at the method in which the height of lack of penetration can be measured by measuring an object with the ultrasound, determining the beam path length W of an F echo based on the measurement, and applying the beam path length W to a regression equation obtained in advance. In this method, the "beam path length information" is the "beam path length W where the height of the F echo corresponds to the predetermined echo-dividing curve serving as a reference level." The measurement method of this embodiment will be specifically described below.

—Steps of Measurement Method—

<Generation of Dividing Curves of Echo Heights>

In the measurement method of this embodiment, an ultrasonic test is conducted along the following steps, and the dividing curves of echo heights are obtained before the measurement of an object. The measurement method of this embodiment complies with JIS Z 3060 (2002) "Method for Ultrasonic Examination for Welds of Ferritic Steel."

An ultrasonic flaw detector complying with JIS Z 2352 is used. A probe B5K10×10A70 is used as an example probe. This probe includes a transducer having the dimensions of 10 mm×10 mm. The frequency of the ultrasound applied from the probe to a standard test piece is 5 MHz. The reflection angle is 70°.

An standard test piece STB-A1 is used as a standard test piece. A test piece RB-41 No. 1 is used as a comparison test piece. Glycerin paste or water is used as a coupling medium applied between each test piece and the probe.

First, the probe index and the refraction angle are measured, and the time base is adjusted, by using the standard test piece, STB-A1.

Figure 2:
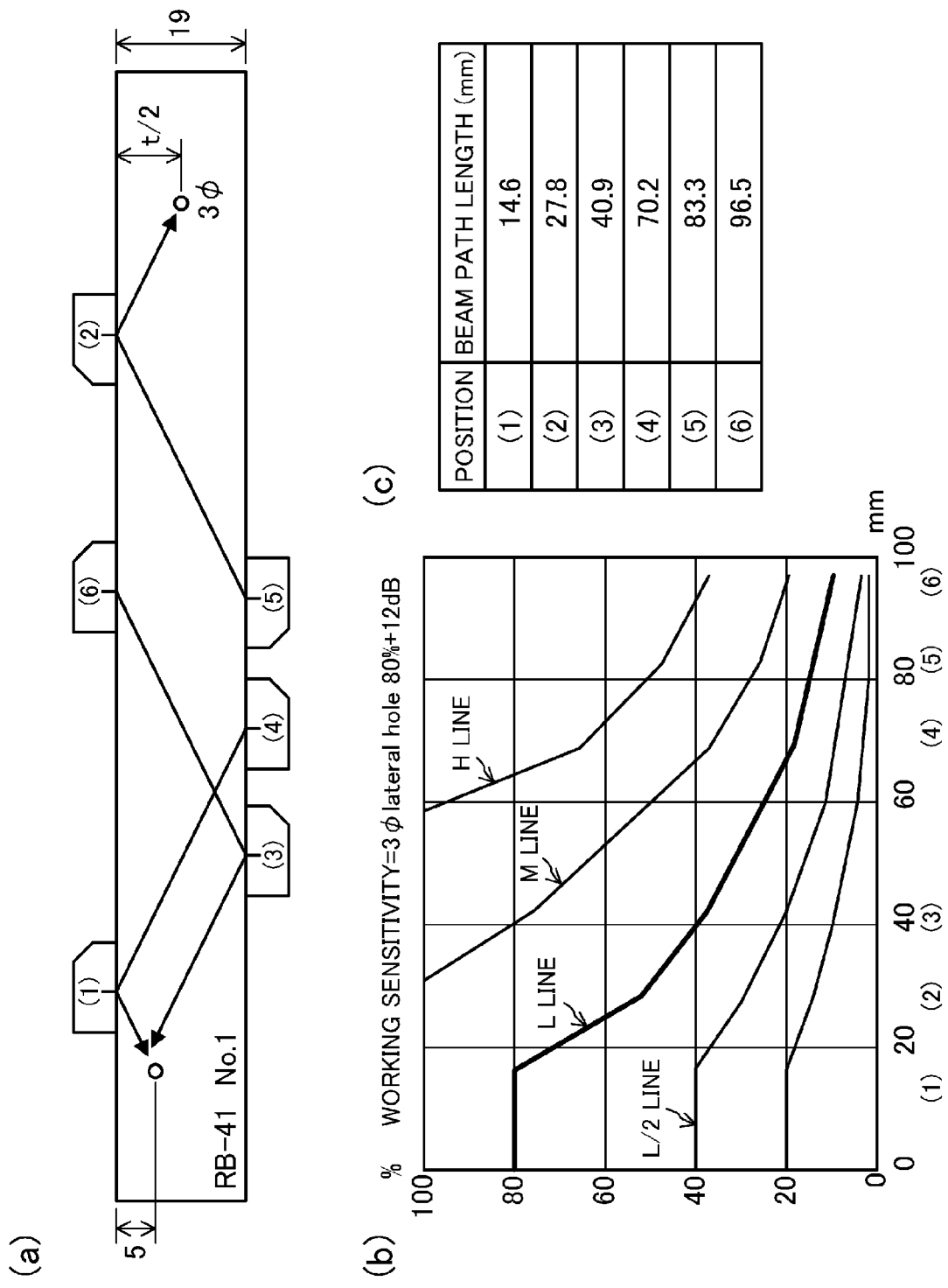
FIG. 2(a) is a cross-sectional view schematically showing a test piece (RB-41 No. 1) used in a measurement method of one embodiment of the present disclosure.
FIG. 2(b) is a graph showing dividing curves of echo heights obtained from the test piece illustrated in FIG. 2(a).
FIG. 2(c) is a table showing relations between the positions of the test pieces illustrated in FIG. 2 (a) and the beam path lengths.
Figure 3:
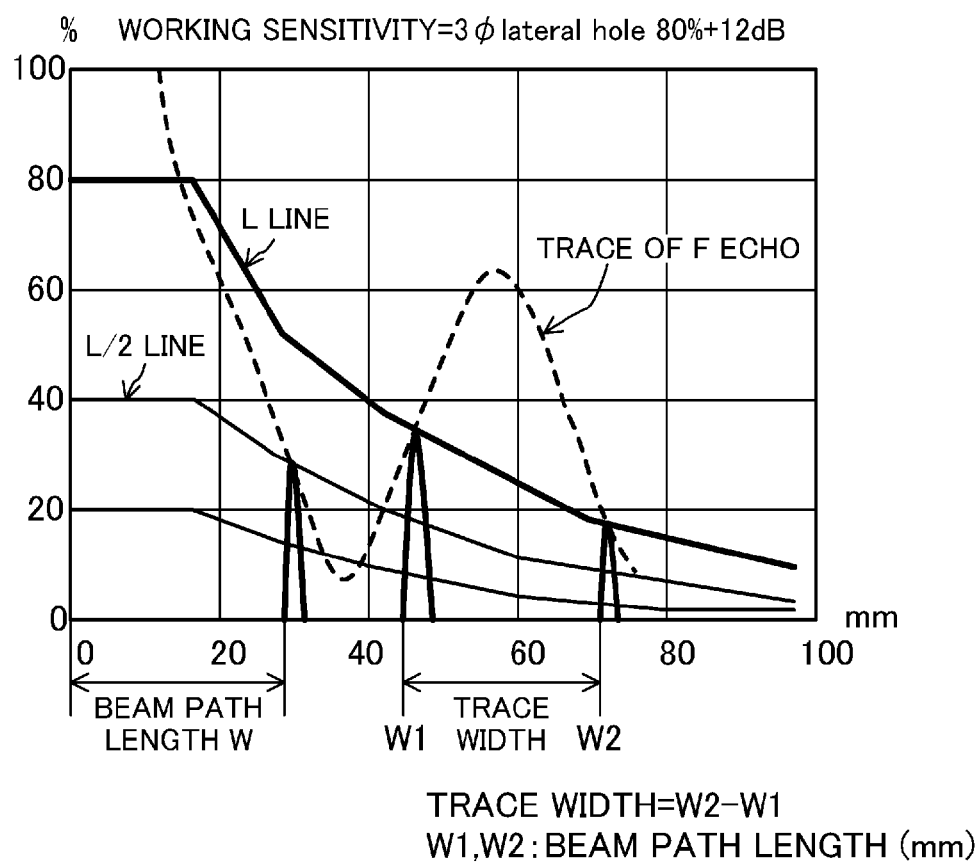
FIG. 3 is a graph showing the dividing curves of echo heights obtained from the predetermined test piece, and a trace of an F echo returned to a probe.

Next, probes are disposed in turn at positions (1)-(6) on an upper surface and a back surface of the test piece RB-41 No. 1 as illustrated in FIG. 2(*a*). Then, the ultrasound is applied to the test piece RB-41 No. 1 at a predetermined refraction angle (70° in this embodiment) so that the echo height is measured in a predetermined reference hole. Here, the maximum echo heights measured in the reference hole having a diameter of 3 mm are plotted relative to the beam path length to form an H line, which serves as a reference working sensitivity. An M line indicates values lower by 6 dB than the H line does. An L line indicates values lower by 6 dB than the M line does. An L/2 line indicates values lower by 6 dB than the L line does. In this manner, the dividing curves of echo heights in FIG. 2(*b*) are obtained.

<Formulation of Regression Equation>

Figure 9:
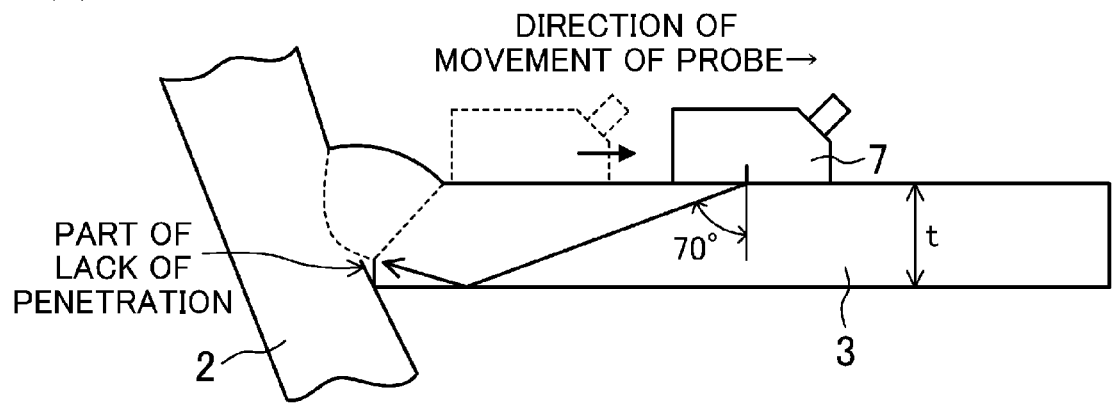
FIG. 9(a) illustrates how a probe is moved forward or backward to scan a U-shaped rib.
FIG. 9(b) is a graph showing the beam path length based on a measurement of an object.
Figure 9:
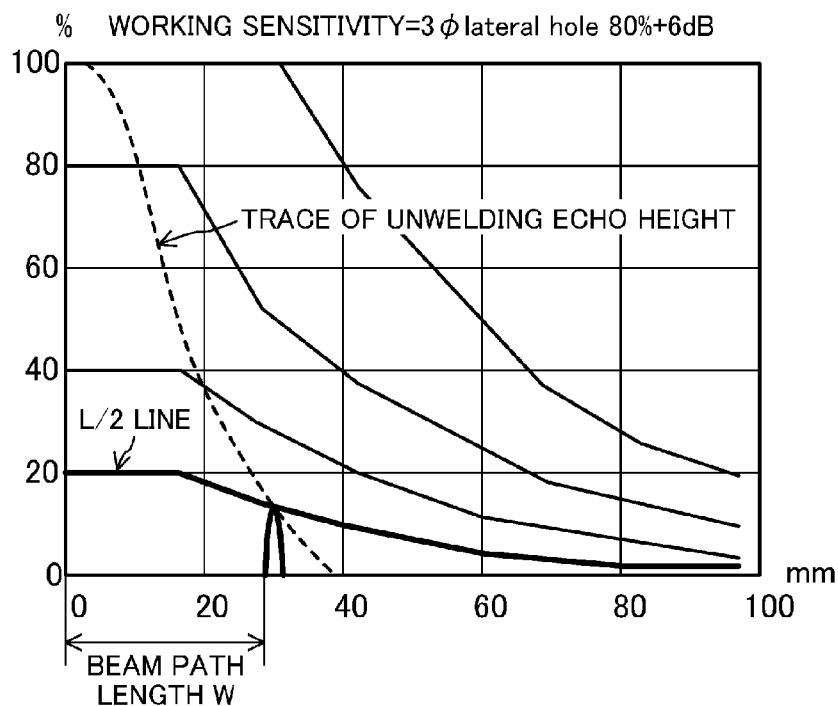

A plurality of weld test samples are measured with the ultrasound by using a probe 7 moved forward or backward to scan a U-shaped rib 3 so that an ultrasonic beam is directed toward a weld line at a right angle. The plurality of weld test samples each include the U-shaped rib 3 and a deck plate 2 as illustrated in FIG. 9(*a*), and have different heights of lack of penetration. In moving the probe 7 for scanning, the flaw detection skip distance is in the range from 0.5 skip distance to 1 skip distance. The height of an F echo that is applied from the probe 7 to the weld line at a predetermined refraction angle (e.g., 70°), reflected by a part of lack of penetration of a weld, and returned to the probe 7 is measured. The U-shaped rib 3 has the same thickness as the U-shaped rib to be measured does, i.e., a thickness of 6 mm.

As shown in FIG. 9(*b*), the beam path length W where the height of the F echo corresponds to a predetermined echo-dividing curve serving as a reference level is determined.

Then, a regression equation is formulated based on a relation between the beam path length W and the height of lack of penetration. In the example in FIG. 9(b), the L/2 line of the dividing curves of echo heights is used as a reference level. The reference level is not limited to the L/2 line, and any reference level may be determined as long as the reference level enables precise estimation of the height of lack of penetration. In FIG. 9(b), a broken line represents a variation of the height of the F echo observed by the probe 7 in scanning.

Figure 10:
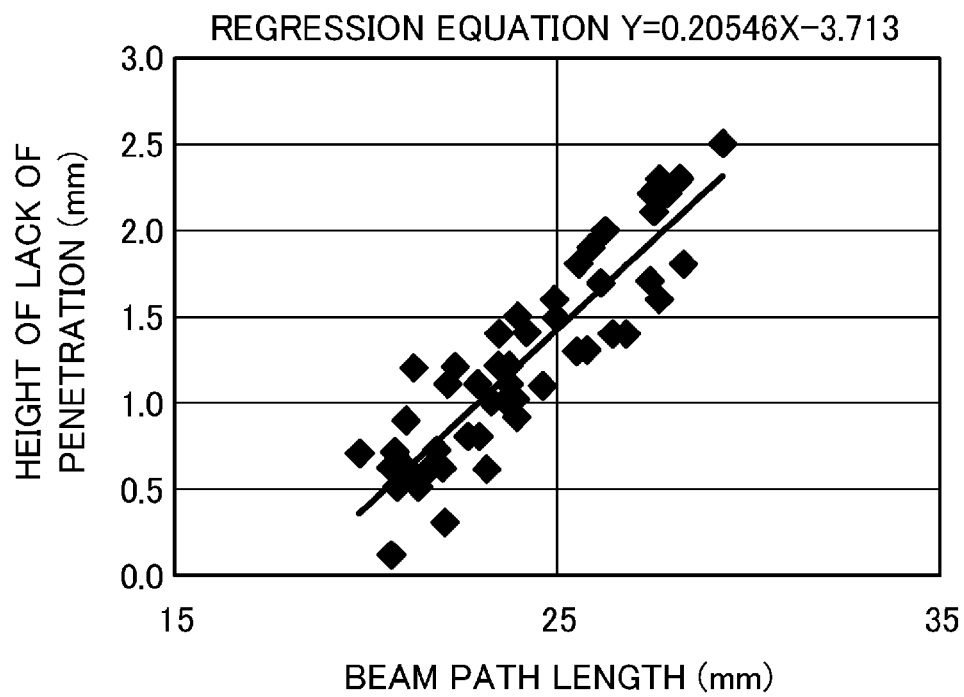
FIG. 10 is a graph showing an example regression equation showing a relation between the height of lack of penetration (mm) and the beam path length (mm) obtained when the U-shaped rib has a thickness of 6 mm and an L/2 line is used as a reference level.

FIG. 10 is a graph showing an example regression equation showing a relation between the height of lack of penetration (mm) and the beam path length W (mm) where the U-shaped rib has a thickness of 6 mm and the height of the F echo corresponds to the L/2 line. This regression equation can be obtained by plotting the measurements and then using, e.g., the least square method.

<Measurement of Height of Lack of Penetration/Pass-Fail Determination>

Next, as illustrated in FIG. 9(a), to scan the U-shaped rib 3 of the target steel plate floor 1 to be measured, the probe 7 is moved forward or backward so that an ultrasonic beam is directed toward a weld line at a right angle. Then, the height of an F echo applied from the probe 7 to the weld line at a predetermined refraction angle, reflected by a part of lack of penetration, and returned to the probe is measured. Here, in moving the probe 7 for scanning, the flaw detection skip distance is in the range from about 0.5 skip distance to 1 skip distance. The measurement starts being made with the probe 7 from a position as close to the weld as possible, and then the probe 7 is moved in a direction away from the weld. This enables easy determination of the beam path length if an unskilled operator makes measurements.

Next, the beam path length W where the height of the measured F echo decreases to a reference level that is the L/2 line of the dividing curves of echo heights in FIG. 2(b) is determined. Subsequently, the height of lack of penetration in the weld of the steel plate floor 1 can be calculated by applying the beam path length W obtained as above to the regression equation shown in FIG. 10. If the regression equation is $Y=0.20546X-3.713$, the height of lack of penetration can be calculated as approximately 1.42 mm, where the beam path length W is, e.g., 25 mm.

Finally, it is determined whether the calculated height of lack of penetration satisfies a predetermined criterion. According to the specifications for highway bridges, the criterion of the depth of partial penetration of the target steel plate floor 1 is 75% or more of the thickness of the U-shaped rib. If the U-shaped rib 3 is 6 mm in thickness, the steel plate floor 1 having a weld in which the height of lack of penetration is 1.5 mm or less is determined to be passed, and the steel plate floor 1 having a weld in which the height of lack of penetration is more than 1.5 mm is determined to be failed.

The target object to be measured in the measurement method of this embodiment is not limited to the steel plate floor. Any structure created by welding is applicable.

—Advantages of Measurement Method—

The measurement method of this embodiment allows calculation of the height of lack of penetration in a weld based on the measurement of an actually welded product, and enables pass/fail determination of the depth of partial penetration of every product. Thus, highly reliable products can be released, and bridges in which fatigue cracks are unlikely to be formed can be constructed. For example, the dividing curves of echo heights and the regression equation used for the measurement, and the measurements of the target steel plate floor 1 to be measured are stored as data, which can be used to review the test results.

The shape of a penetrating portion of a weld root varies. For this reasons, in the methods of Patent Documents 1 and 2 where the measurement is conducted with the probe 7 disposed at a fixed position, a reflection echo having a proper height might not be obtained. In contrast, in the method of this embodiment, the probe 7 is moved forward or backward to scan the U-shaped rib 3 (the first member) for the measurement, and thus the height of lack of penetration can be precisely calculated.

The measurement with the method of this embodiment has showed that even if the U-shaped rib 3 is 6 mm in thickness, the measurement error of the height of lack of penetration can fall within approximately ±0.5 mm. The height of lack of penetration can be immediately obtained from the beam path length by using the regression equation, and thus the depth of partial penetration can be quickly obtained.

In the measurement method of this embodiment, the height of lack of penetration can be measured without a B echo of which the measured value is unstable. Thus, the method of this embodiment enables the measurement with higher precision than the methods in which the ratio between a B echo and an F echo is used.

As described above, the measurement method of this embodiment complies with JIS Z 3060 (2002) "Method for Ultrasonic Examination for Welds of Ferritic Steel." In the measurement method of this embodiment, the devices and standard test pieces provided in JIS can be used without special facilities. The measurement might be made with a dedicated ultrasonic flaw detector that stores programs etc. for implementing the method. Alternatively, the measurement may be made with a general ultrasonic flaw detector, and a personal computer etc. may be used to undergo processes, such as imaging of the measurement.

—Example of Modification to Thickness of U-Shaped Rib—

The measurement method of the embodiment where the U-shaped rib welded to the deck plate 2 is 6 mm in thickness has been described. Even if the U-shaped rib 3 has a modified thickness, the depth of partial penetration of a weld can be measured under a similar method. Measurement steps where the U-shaped rib 3 is 8 mm in thickness will be described below.

First, the dividing curves of echo heights shown in FIG. 2(b) are obtained according to a similar method in which the test piece and devices used for the U-shaped rib 3 that is 6 mm in thickness are used.

Next, a plurality of weld test samples are measured with the ultrasound by using a probe 7 moved forward or backward to scan a U-shaped rib 3 so that an ultrasonic beam is directed toward a weld line at a right angle. The plurality of weld test samples each include the U-shaped rib 3 and a deck plate 2, and have different heights of lack of penetration. In moving the probe 7 for scanning, the flaw detection skip distance is in the range from about 0.5 skip distance to 1 skip distance. Here, the height of an F echo that is applied from the probe 7 to the weld line at a predetermined refraction angle (e.g., 70°), reflected by a part of lack of penetration of a weld, and returned to the probe 7 is measured.

Subsequently, the beam path length W where the height of the F echo of the weld test sample is equal to a reference level is determined, and then a regression equation is formulated based on a relation between the beam path length W and the height of lack of penetration. Here, the L/2 line of the dividing curves of echo heights is used as the reference level to determine the beam path length W. The reference level is not limited to the L/2 line, and any reference level may be determined as long as the reference level enables precise estimation of the height of lack of penetration.

Figure 11:
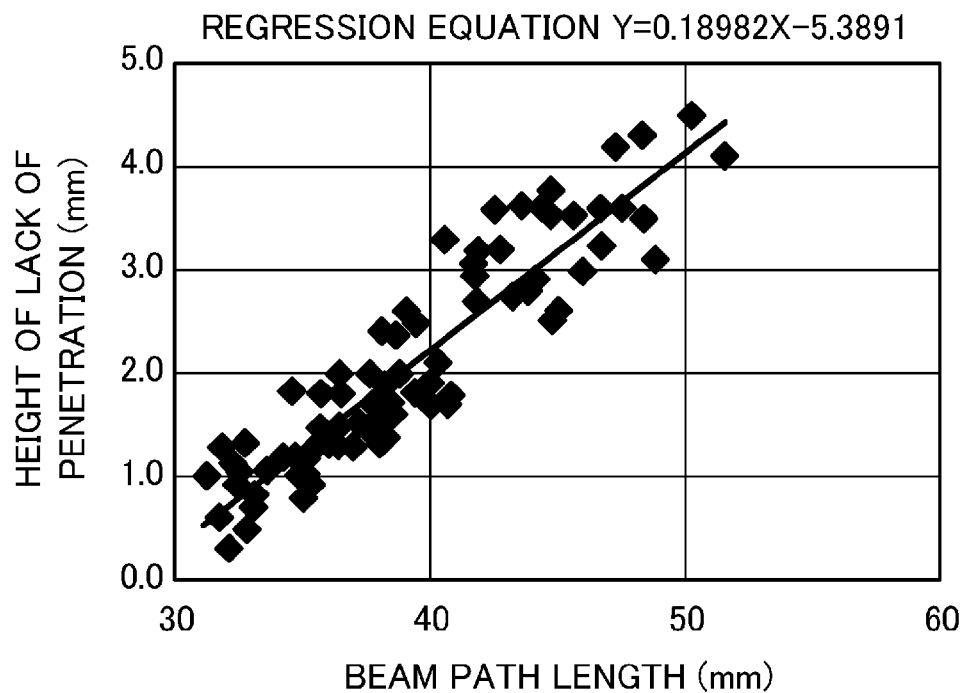
FIG. 11 is a graph showing an example regression equation showing a relation between the height of lack of penetration (mm) and the beam path length (mm) obtained when a U-shaped rib has a thickness of 8 mm and an L/2 line is used as a reference level.

FIG. 11 is a graph showing an example regression equation showing a relation between the height of lack of penetration (mm) and the beam path length W (mm) where the U-shaped rib has a thickness of 8 mm.

Next, as illustrated in FIG. 9(a), to scan the U-shaped rib 3 of the target steel plate floor 1 to be measured, the probe 7 is moved forward or backward so that an ultrasonic beam is directed toward a weld line at a right angle. Then, the height of an F echo applied from the probe 7 to the weld line at a predetermined refraction angle, reflected by a part of lack of penetration, and returned to the probe is measured. Here, in moving the probe 7 forward or backward for scanning, the flaw detection skip distance is in the range from 0.5 skip distance to 1 skip distance. The measurement starts being made with the probe 7 at a position as close to the weld as possible, and then the probe 7 is moved in a direction away from the weld. This enables easy determination of the beam path length information.

Next, the beam path length W where the height of the measured F echo is equal to a reference level that is the L/2 line of the dividing curves of echo heights in FIG. 2(b) is determined. Subsequently, the height of lack of penetration in the weld of the steel plate floor 1 can be calculated by applying the beam path length W obtained as above to the regression equation shown in FIG. 11.

Finally, it is determined whether the calculated height of lack of penetration satisfies a predetermined criterion. According to the specifications for highway bridges, the criterion of the depth of partial penetration of the target steel plate floor 1 to be measured is 75% or more of the thickness of the U-shaped rib. If the U-shaped rib 3 is 8 mm in thickness, the steel plate floor 1 having a weld in which the height of lack of penetration is 2.0 mm or less is determined to be passed, and the steel plate floor 1 having a weld in which the amount of welding is more than 2.0 mm is determined to be failed.

As described above, the measurement method of this embodiment enables precise measurements of the height of lack of penetration and the depth of partial penetration even if the U-shaped rib 3 is 8 mm in thickness. In this manner, the thickness of the U-shaped rib 3 is not limited to a particular thickness in the measurement method of this embodiment. The method of this embodiment can be used by determining a regression equation corresponding to the thickness of the U-shaped rib 3 as long as the thickness of the U-shaped rib 3 is within the range in which the reflection echo having an adequate height can be observed.

—Example of Modification to Reference Level—

In the measurement method of this embodiment, the reference level for determining the beam path length W may be appropriately modified in consideration of the height of the F echo or the noise level. In the following example, the height of lack of penetration is calculated with a reference level that is different from that of the above-described example where the U-shaped rib 3 is 8 mm in thickness.

First, dividing curves of echo heights shown in FIG. 2(b) are obtained according to a similar method where the same test piece and devices as those in the above-described example are used.

Next, a plurality of weld test samples are measured with the ultrasound by using a probe 7 moved forward or backward to scan on a U-shaped rib 3 so that an ultrasonic beam is directed toward a weld line at a right angle. The plurality of weld test samples each include the U-shaped rib 3 and a deck plate 2, and have different heights of lack of penetration. Here, the height of an F echo that is applied from the probe 7 to the weld line at a predetermined refraction angle (e.g., 70°), reflected by a part of lack of penetration of a weld area, and returned to the probe 7 is measured.

Figure 12:
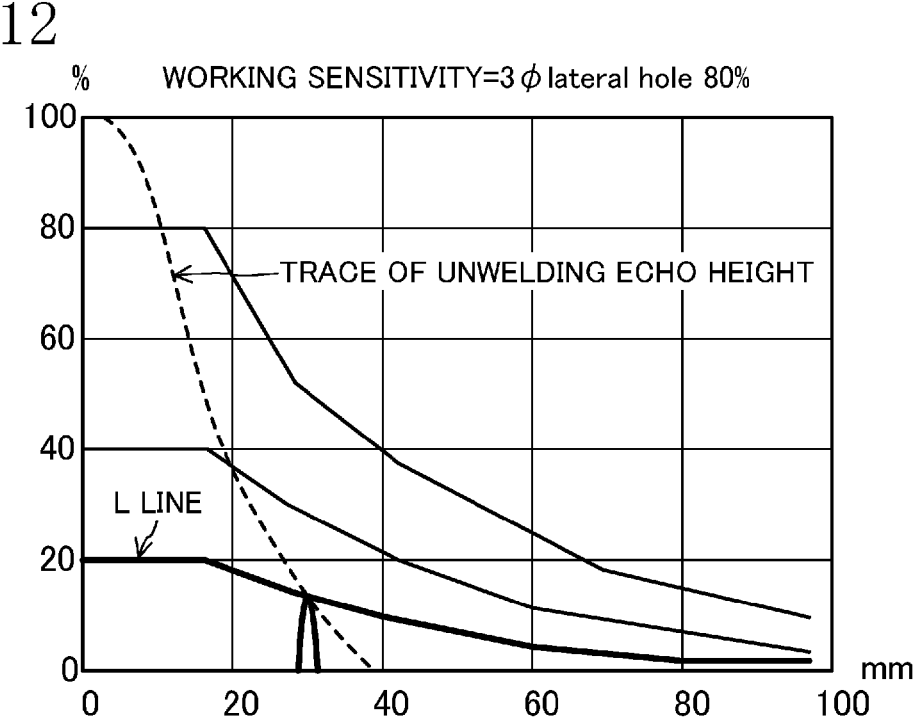
FIG. 12 is a graph showing the beam path length based on a measurement of an object.

Subsequently, as shown in FIG. 12, the beam path length W where the height of the F echo of the weld test sample is equal to a reference level is determined, and then a regression equation is formulated based on a relation between the beam path length W and the height of lack of penetration. Here, the L line of the dividing curves of echo heights is used as the reference level for determining the beam path length W.

Figure 13:
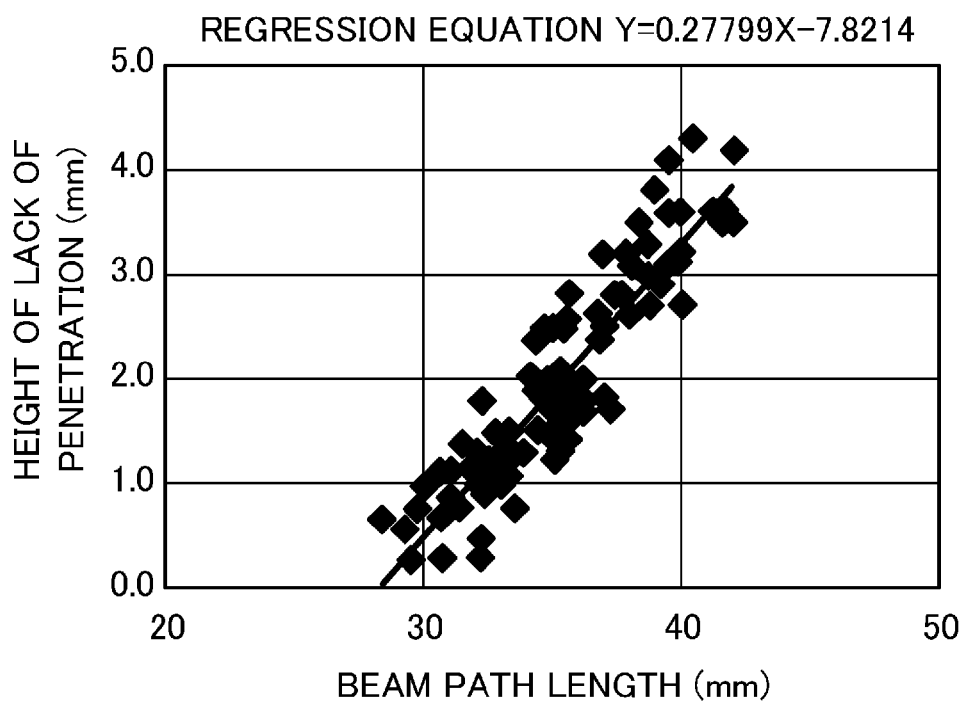
FIG. 13 is a graph showing an example regression equation showing a relation between the height of lack of penetration (mm) and the beam path length (mm) obtained when a U-shaped rib has a thickness of 8 mm and an L line is used as a reference level.

FIG. 13 is a graph showing an example regression equation showing a relation between the height of lack of penetration (mm) and the beam path length W (mm) where the U-shaped rib has a thickness of 8 mm, and the L line is used as the reference level.

Next, as illustrated in FIG. 9(a), to scan the U-shaped rib 3 of the target steel plate floor 1 to be measured, the probe 7 is moved forward or backward so that an ultrasonic beam is directed toward a weld line at a right angle. Then, the height of an F echo applied from the probe 7 to the weld line at a predetermined refraction angle, reflected by a part of lack of penetration, and returned to the probe is measured. Here, in moving the probe 7 forward or backward for scanning, the flaw detection skip distance is in the range from 0.5 skip distance to 1 skip distance. The measurement starts being made with the probe 7 at a position as close to the weld as possible, and then the probe 7 is moved in a direction away from the weld.

Next, the beam path length W where the height of the measured F echo is equal to a reference level that is the L line of the dividing curves of echo heights in FIG. 2(b). Subsequently, the height of lack of penetration in the weld of the steel plate floor 1 can be calculated by applying the beam path length W obtained as above to the regression equation shown in FIG. 13.

Finally, it is determined whether the calculated height of lack of penetration satisfies a predetermined criterion according to a method similar to that in the case where the L/2 line is used as the reference level.

As described above, in the measurement method of this embodiment, two or more echo-dividing curves can be used to calculate the beam path length W. The choice of the line as the reference level depends on the measurement conditions etc. The criterion of whether the target object is passed or failed depends on the object to be measured.

—Ultrasonic Flaw Detector—

An ultrasonic flaw detector used in a method for measuring the depth of partial penetration of a weld part according to this embodiment is similar to the ultrasonic flaw detector of the first embodiment shown in FIG. 8(a) except some of the functions. Thus, the ultrasonic flaw detector of this embodiment will be described below with reference to FIGS. 8(a) and 8(b).

As shown in FIG. 8(a), the ultrasonic flaw detector 11 of this embodiment includes the probe 7, a flaw detection unit (a pulser receiver) 13, an AD conversion unit 15, a signal storage unit 19, a memory 29, an unit for calculating height of lack of penetration 17, and a determining unit 21. The probe 7 applies the ultrasound to an object. The flaw detection unit 13 controls operation of the probe 7, and measures a beam path length and the height of F echo of the ultrasound reflected in the object and returned to the probe 7. The AD conversion unit 15 converts a value measured by the flaw detection unit 13 to a digital value. The signal storage unit 19 stores the measured value converted by the AD conversion unit 15. The memory 29 stores data about the dividing curves of echo heights, and the data about a regression equation showing the relation between the beam path length information and the height of lack of penetration. Based on the measured values stored in the signal storage unit 19 and the data stored in the memory 29, the unit for calculating height of lack of penetration 17 calculates the beam path length information such as the beam path length W, and the height (the height of lack of penetration) of the part of lack of penetration of the weld between the target U-shaped rib (the first member) to be measured and the deck plate (the second member). The determining unit 21 determines whether the weld is passed or failed based on the height of lack of penetration calculated by the unit for calculating height of lack of penetration 17.

The ultrasonic flaw detector 11 may further include an image processing unit 23 and a display unit 25. The image processing unit 23 performs image processing on the data about the height of lack of penetration calculated by the unit for calculating height of lack of penetration 17. The display unit 25 displays the data about the height of lack of penetration on which the image processing has been performed.

The probe 7 is disposed on a predetermined surface of a target object with glycerin or water interposed therebetween. In the above-described measurement method, the measurement is made at a refraction angle of 70°. The probe 7 may be a part of the ultrasonic flaw detector 11, or may be connected, as an independent member, with the ultrasonic flaw detector 11.

The signal storage unit 19 is, e.g., a publicly known memory. In the above-described measurement method, the signal storage unit 19 stores digitized values etc. of a target object. The memory 29 stores data about each dividing curve of echo heights. The memory 29 also stores, for example, data about the beam path length information such as the beam path length of a target object to be tested or measured, data about the regression equation obtained from the beam path length information such as the beam path length, data about the height of lack of penetration calculated by the unit for calculating height of lack of penetration 17.

The unit for calculating height of lack of penetration 17 determines, as the beam path length information, the beam path length W in which the height of the F echo that is applied to a weld line between the first member (the U-shaped rib) and the second member (the deck plate) at a predetermined refraction angle, reflected by a part of lack of penetration of a weld, and returned to the probe 7 is equal to the reference level shown in the dividing curves of echo heights when the probe 7 is moved forward or backward to scan an object so that an ultrasonic beam is directed toward the weld line at a right angle. These data are stored as the data obtained at the measurement positions arranged along the longitudinal direction of the target object.

Next, the unit for calculating height of lack of penetration 17 determines the beam path length W from the measured height of an F echo that is applied from the probe 7 to a weld line between the first member (the U-shaped rib) and the second member (the deck plate) at a predetermined refraction angle, reflected by a part of lack of penetration, and returned to the probe 7 when the probe 7 is moved forward or backward to scan the first member so that an ultrasonic beam is directed toward the weld line at a right angle. To calculate the height of lack of penetration, the unit for calculating height of lack of penetration 17 also applies the beam path length W to the regression equation formulated in advance based on the relation between the beam path length W and the height of lack of penetration. A program for automatically performing these calculations may be stored in advance in a memory etc. (another memory different from the memory 29) of the ultrasonic flaw detector 11. Alternatively, the hardware may be configured to allow the unit for calculating height of lack of penetration 17 to perform the calculations.

The determining unit 21 determines that the weld is failed if a measured value calculated by the unit for calculating height of lack of penetration 17 exceeds a reference value determined in advance depending on the target object. Then, the determining unit 21 outputs, e.g., a signal indicating that the weld is failed. The determining unit 21 also determines that the target object is passed if the measured value is less than or equal to the predetermined reference value. Then, the determining unit 21 outputs, e.g., a signal indicating that the target object is passed. The ultrasonic flaw detector 11 may be configured to sound an alarm if the target object is determined to be failed, or to mark the failed target object. The ultrasonic flaw detector 11 may be configured to perform processes until the calculation of the height of lack of penetration without providing the determining unit 21.

When the height of lack of penetration in the target object (the U-shaped rib in this embodiment) is measured along the longitudinal direction (i.e., the extension direction of the weld line) of the target object at predetermined intervals, the data about the measurements are stored in the signal storage unit 19. In this case, the image processing unit 23 produces a graph representing the calculated height of lack of penetration and the positional information (information about the location at which the measurement was made along the extension direction of the weld line). Specifically, the image processing unit 23 outputs image data showing the height of lack of penetration calculated at a plurality of measurement points arranged along the extension direction of the weld line. The image data are provided for each of the plurality of measurement points. Based on the image data, the display unit 25 displays the height of lack of penetration for each of the points arranged along the weld line in a visually recognizable manner.

FIG. 8(b) is a graph showing example measurements, which are displayed by the display unit 25, at a plurality of measurement points. The display of the measurements of the depth of partial penetration of the weld eases understanding of the measurements. The display unit 25 may not always been provided in the ultrasonic flaw detector 11. The measurements may be displayed on a screen of a computer etc. connected with the ultrasonic flaw detector 11.

The ultrasonic flaw detector 11 of this embodiment enables automatic calculation of the height of lack of penetration, thus reducing human errors. Even if an operator is unskilled in the measurement operation, the beam path length W and the height of lack of penetration can be automatically calculated based on the measurements.

The method for measuring the depth of partial penetration and the ultrasonic flaw detector described above are only examples of embodiments. The measurement conditions of an object, the devices used, the configurations of the ultrasonic flaw detector, etc., can be modified as appropriate without departing from the spirit and scope of the present invention.

The method for measuring the depth of partial penetration according to one embodiment of the present disclosure is useful to increase, e.g., the reliability of infrastructures such as bridges.

DESCRIPTION OF REFERENCE CHARACTERS

1 Steel Plate Floor
2 Deck Plate
3 U-Shaped Rib
5 Weld Bead
7 Probe
11 Ultrasonic Flaw Detector
13 Flaw Detection Unit
15 AD Conversion Unit
17 Unit for Calculating Height of Lack of Penetration
19 Signal Storage Unit
21 Determining Unit
23 Image Processing Unit
25 Display Unit
29 Memory

The invention claimed is:

1. A method for measuring a height of lack of penetration in a weld, the method comprising steps of:
using a probe applying an ultrasonic beam to an object to define a dividing curve of an echo height as a reference level for evaluating a height of an F echo that is reflected by a part of lack of penetration of the weld and returned to the probe;
obtaining beam path length information based on the dividing curve of the echo height and the height of the F echo obtained by moving the probe that applies the ultrasonic beam to the object at a predetermined angle to scan surfaces of a plurality of weld test samples having different heights of lack of penetration, a weld bead being disposed on the surface; and
formulating a regression equation showing a relation between the beam path length information and the height of lack of penetration.

2. The method of claim 1, further comprising steps of:
using the probe applying the ultrasonic beam to an object at the predetermined angle to scan a surface of a first member on which a weld bead is disposed if the first member is welded to a second member;
obtaining the beam path length information based on the height of the F echo and the dividing curve of the echo height; and
applying the beam path length information to the regression equation to calculate the height of lack of penetration in the weld.

3. The method of claim 2, wherein
a range of a beam path length where the height of the F echo exceeds the dividing curve of the echo height is defined as a trace width, and
the trace width is defined as the beam path length information.

4. The method of claim 3, further comprising steps of:
if the calculated height of lack of penetration exceeds a predetermined reference value, determining that the weld is failed; and
if the height of lack of penetration is less than or equal to the reference value, determining that the weld is passed.

5. The method of claim 2, wherein
a beam path length where the height of the F echo corresponds to the dividing curve of the echo height is defined as the beam path length information.

6. The method of claim 5, further comprising steps of:
if the calculated height of lack of penetration exceeds a predetermined reference value, determining that the weld is failed; and
if the height of lack of penetration is less than or equal to the reference value, determining that the weld is passed.

7. The method of claim 2, further comprising steps of:
if the calculated height of lack of penetration exceeds a predetermined reference value, determining that the weld is failed; and
if the height of lack of penetration is less than or equal to the reference value, determining that the weld is passed.

8. The method of claim 2, wherein
the second member is a deck plate forming a steel plate floor, and
the first member is a rib welded to one of surfaces of the deck plate and having a U-shaped cross section.

9. The method of claim 8, further comprising steps of:
if the calculated height of lack of penetration exceeds a predetermined reference value, determining that the weld is failed; and
if the height of lack of penetration is less than or equal to the reference value, determining that the weld is passed.

10. The method of claim 1, wherein
a range of a beam path length where the height of the F echo exceeds the dividing curve of the echo height is defined as a trace width, and
the trace width is defined as the beam path length information.

11. The method of claim 1, wherein
a beam path length where the height of the F echo corresponds to the dividing curve of the echo height is defined as the beam path length information.

12. An ultrasonic flaw detector, comprising:
a probe configured to apply the ultrasound to an object;
a flaw detection unit configured to control operation of the probe, and to measure a beam path length and a height of an F echo of the ultrasound reflected by a part of lack of penetration of the object, and returned to the probe;
an AD conversion unit configured to convert a value measured by the flaw detection unit to a digital value;
a signal storage unit configured to store the measured value converted by the AD conversion unit;
a memory configured to store data about a dividing curve of an echo height, and data about a regression equation showing a relation between beam path length information and a height of lack of penetration; and
a computer processing unit configured to:
obtain the beam path length information based on the measured value stored in the signal storage unit and the data stored in the memory, and
calculate height of lack of penetration in a weld between a first member and a second member that form the object, said calculation being based on the beam path length information and the regression equation stored in the memory.

13. The ultrasonic flaw detector of claim 12, wherein the computer processing unit is further configured to:
determine, as the beam path length information, a trace width that is a range of a beam path length where the height of the F echo returned to the probe on the first member exceeds the dividing curve of the echo height, and
apply the trace width to the regression equation to calculate the height of lack of penetration.

14. The ultrasonic flaw detector of claim 13, further comprising a determining unit configured to:

determine that the weld is failed if the height of lack of penetration calculated exceeds a predetermined reference value, and determine that the weld is passed if the height of lack of penetration is less than or equal to the reference value.

15. The ultrasonic flaw detector of claim 13, further comprising:

an image processing unit configured to output image data showing a height of lack of penetration calculated at a plurality of measurement points arranged along a longitudinal direction of the first member, the image data being provided for each measurement point; and a display unit configured to display the height of lack of penetration for each measurement point based on the image data.

16. The ultrasonic flaw detector of claim 12, wherein the computer processing unit is further configured to:

determine, as the beam path length information, a beam path length where the height of the F echo returned to the probe on the first member corresponds to the dividing curve of echo height, and apply the beam path length to the regression equation to calculate the height of lack of penetration.

17. The ultrasonic flaw detector of claim 16, further comprising a determining unit configured to:

determine that the weld is failed if the height of lack of penetration calculated exceeds a predetermined reference value, and determine that the weld is passed if the height of lack of penetration is less than or equal to the reference value.

18. The ultrasonic flaw detector of claim 16, further comprising:

an image processing unit configured to output image data showing a height of lack of penetration calculated at a plurality of measurement points arranged along a longitudinal direction of the first member, the image data being provided for each measurement point; and a display unit configured to display the height of lack of penetration for each measurement point based on the image data.

19. The ultrasonic flaw detector of claim 12, further comprising a determining unit configured to:

determine that the weld is failed if the height of lack of penetration calculated exceeds a predetermined reference value, and determine that the weld is passed if the height of lack of penetration is less than or equal to the reference value.

20. The ultrasonic flaw detector of claim 19, further comprising:

an image processing unit configured to output image data showing a height of lack of penetration calculated at a plurality of measurement points arranged along a longitudinal direction of the first member, the image data being provided for each measurement point; and a display unit configured to display the height of lack of penetration for each measurement point based on the image data.

21. The ultrasonic flaw detector of claim 12, further comprising:

an image processing unit configured to output image data showing a height of lack of penetration calculated at a plurality of measurement points arranged along a longitudinal direction of the first member, the image data being provided for each measurement point; and a display unit configured to display the height of lack of penetration for each measurement point based on the image data.

* * * * *